(12) United States Patent
Krohmann et al.

(10) Patent No.: US 10,039,849 B2
(45) Date of Patent: Aug. 7, 2018

(54) PLASMA-GENERATED GAS STERILIZATION METHOD AND DEVICE

(71) Applicant: LEIBNIZ-INSTITUT FUER PLASMAFORSCHUNG UND TECHNOLOGIE E.V., INP GREIFSWALD, Greifswald (DE)

(72) Inventors: Udo Krohmann, Neubrandenburg (DE); Joerg Ehlbeck, Hinrichshagen (DE); Torsten Neumann, Neubrandenburg (DE); Uta Schnabel, Greifswald (DE); Mathias Andrasch, Stralsund (DE); Wolfram Lehmann, Neuenkirchen (DE); Klaus-Dieter Weltmann, Binz (DE)

(73) Assignee: LEIBNIZ-INSTITUT FUER PLASMAFORSCHUNG UND TECHNOLOGIE E. V., INP GREIFSWALD, Greifswald (DE)

(*) Notice: Subject to any disclaimer, the term of this patent is extended or adjusted under 35 U.S.C. 154(b) by 0 days.

(21) Appl. No.: 15/487,483

(22) Filed: Apr. 14, 2017

(65) Prior Publication Data

US 2017/0216469 A1    Aug. 3, 2017

Related U.S. Application Data

(63) Continuation-in-part of application No. 13/696,723, filed as application No. PCT/EP2011/057402 on May 9, 2011, now Pat. No. 9,623,132.

(30) Foreign Application Priority Data

May 7, 2010  (DE) ......................... 10 2010 019 863

(51) Int. Cl.
*A61L 2/14*    (2006.01)

(52) U.S. Cl.
CPC ............. *A61L 2/14* (2013.01); *A61L 2202/11* (2013.01)

(58) Field of Classification Search
CPC ....................................................... A61L 2/14
See application file for complete search history.

(56) References Cited

U.S. PATENT DOCUMENTS

| 5,451,259 A | * | 9/1995 | Krogh .................... B01J 12/002 |
| | | | 118/723 MR |
| 5,633,424 A | | 5/1997 | Graves et al. |

(Continued)

FOREIGN PATENT DOCUMENTS

| DE | 198 27 442 | | 12/1998 |
| GB | 2302654 | * | 11/1993 |

(Continued)

OTHER PUBLICATIONS

Ono et al. "Measurement of gas temperature and OH density in the afterglow of pulsed positive corona discharge." 2008 J. Phys. D: Appl. Phys. 41.*

(Continued)

*Primary Examiner* — Donald R Spamer
(74) *Attorney, Agent, or Firm* — JMB Davis Ben-David (57) ABSTRACT

The invention relates to a method and to a device for quickly decontaminating and sterilizing preferably thermolabile goods using a plasma gas that is preferably generated from air as a process gas, with the subsequent humidification of said plasma gas with water. The method comprises the following steps: generating a plasma from air as the process gas, which forms reactive nitrogen and oxygen species; oxidizing NO to form $NO_2$ at temperatures below 400° C. so that a plasma-activated gas mixture forms having an $NO_2$ content of at least 0.3%; bringing said plasma-activated gas mixture in contact with water in one or more of the states of (Continued)

aggregation thereof; bringing the latter gas mixture in contact with the objects to be decontaminated or sterilized.

13 Claims, 8 Drawing Sheets

(56) References Cited

U.S. PATENT DOCUMENTS

| | | |
|---|---|---|
| 5,869,000 A | 2/1999 | DeCato |
| 5,920,799 A | 7/1999 | Graves et al. |
| 6,096,564 A * | 8/2000 | Denes .................... A61L 2/14 438/1 |
| 2005/0058569 A1 | 3/2005 | Perlov et al. |
| 2006/0027539 A1 | 2/2006 | Golkowski |
| 2008/0237484 A1 | 10/2008 | Morfill et al. |
| 2008/0317626 A1* | 12/2008 | Arnold ................. A61L 2/0094 422/29 |
| 2010/0254853 A1* | 10/2010 | Lee ........................ A61L 2/14 422/29 |

FOREIGN PATENT DOCUMENTS

| | | |
|---|---|---|
| WO | 96 21473 | 7/1996 |
| WO | 2005 023319 | 3/2005 |

OTHER PUBLICATIONS

Vidmar et al. Plasma Cloaking: Air Chemistry, Broadband Absorption, and Plasma Generation. Remote Measurement Laboratory. SRI International. Feb. 1990.

"Nitrogen Dioxide" Wikipedia. Archived version from May 6, 2010.

Odo et al. Measurement of gas temperature and OH density in the afterglow of pulsed positive corona discharge. J. Phys. D:Appl. Phys. 41 (2008).

Singh, M. K. et al, "Study of Inactivation Factors in Low Temperature Surface-wave Plasma Sterilization," Transactions of the Institute of Electrical Engineers of Japan, vol. 129, No. 1, pp. 30 to 34, (Jan. 1, 2009).

* cited by examiner

TABLE 1

Reduction factors of vegetative/sporulated microorganisms after various times of action of the plasma-activated gas mixture

| Microorganism | Gas | Tyvek | \multicolumn{9}{c|}{Reduction factors (log CFU/mL) after time of action in seconds} |
| | | | 10 | 20 | 30 | 60 | 300 | 600 | 900 | 1800 | 3600 |
|---|---|---|---|---|---|---|---|---|---|---|---|
| *E. coli* | Air | | | | | | >2 | >4 | >6 | >6 | >6 |
|  | Air | x | | | | | >1 | >1.5 | >3 | >5 | >6 |
| *S. aureus* | Air | | | | | | >4 | >5 | >6 | >6 | >6 |
| Conidiospores of *A. brasiliensis* | Air | x | | | | | >1.5 | >2 | >2 | >6 | >6 |
| Endospores of *B. atrophaeus* | Air | | | | | | >2 | >2 | >3 | >6 | >6 |
|  | Air/H$_2$O | | >6 | >6 | >6 | >6 | | | | | |
|  | NO | | | | | | <1 | | | | |
|  | NO/H$_2$O | | | | >1 | | | | | | |
|  | NO$_2$/H$_2$O | | >6 | >6 | >6 | | | | | | |

PLASMA-GENERATED GAS STERILIZATION METHOD AND DEVICE

CROSS REFERENCE TO RELATED APPLICATIONS

This is a Continuation in Part of co-pending U.S. patent application Ser. No. 13/696,723, filed Feb. 20, 2013, which is the US National Stage of International Patent Application No. PCT/EP2011/57402, filed May 9, 2011, which claimed priority to Germany Patent Application No. 10 2010 019 863.3, filed May 7, 2010. The contents of the foregoing patent applications are incorporated by reference herein in their entirety.

FIELD

The invention relates to a method and a device for rapid decontamination and sterilization of preferably thermally labile items using as process gas a plasma gas generated preferably from air and then humidified with water.

BACKGROUND

Known sterilization methods are autoclaving, in other words the use of moist heat, irradiation with ionizing rays, gas sterilization with ethylene oxide (ETO), plasma sterilization and hydrogen peroxide sterilization.

Autoclaving achieves a very good sterilization effect but cannot be used for thermally labile items.

Ethylene oxide (ETO) is a highly toxic gas used for sterilization of thermally labile materials, but it has the disadvantage of relatively long outgassing times of the items to be sterilized, since these outgassing times may be several times longer than the actual treatment time. Because of the toxicity, proper handling of ETO is critical.

Disadvantages of hydrogen peroxide sterilization can be seen primarily in the fact that hydrogen peroxide is a liquid at room temperature. The known methods are based on evaporation of the hydrogen peroxide, but then condensation in the region of the objects to be sterilized must be avoided to ensure that the vapor phase can be extracted completely. The removal of hydrogen peroxide takes place only poorly if large amounts of liquid have accumulated. In this case evaporation is irregular and lasts a long time.

The treatment with ionizing radiation imposes major requirements on equipment and safety. Furthermore, in some cases ionizing radiation may damage the material of the objects being sterilized. The known plasma-sterilization methods do not suffer from these disadvantages or do so to only a limited extent. The sterilizing effect of a plasma depends among other factors on destruction of the germs and biomolecules by the combination of UV and VUV radiation, which destroys the DNA. One disadvantage is that sterilization of heat-sensitive items is usually possible only with increasingly negative pressure.

It has been shown, however, that plasma methods known heretofore have only limited suitability for the treatment or decontamination and sterilization of complex structures, since, for example, the ability of the plasma to penetrate into narrow gaps and lumens is not very good, even under high vacuum.

Another problem is the treatment with sterilizing gases and substances (such as ethylene oxide and hydrogen peroxide), which in higher concentrations are sometimes highly explosive. These methods also require lengthy post-treatment phases to eliminate residues of the highly toxic substances. Thus the storage and handling of these substances are complicated and expensive for the user.

US 2008/0317626 A1 describes a method and a device in which a compound (carbon-based diazenium diolate compound and a powdered acid) that generates a sterile gas is used, in this case to generate preferably NO or a mixture of NO and $NO_2$ as the sterile gas.

US 2010/0166603 A1 describes a sterilization method for powder, using $NO_2$ and moisture as the sterilizing gas. Liquid $NO_2$ is used as the source for gaseous $NO_2$.

A disadvantage of this method is that here also chemical substances are stored and used for formation of the necessary active gases. The times of action necessary are one hour and longer.

WO 2010/022871 describes a non-thermal plasma-sterilization method that describes air among other substances as the carrier gas and uses various additives. $NO_x$ and $H_2O_2$, for example, are mentioned as active species. The use of a non-thermal plasma indeed permits in principle the generation of species with antimicrobial activity and thus also killing kinetics to the extent of several log steps, but a sterilizing effect for the most important reference germs and spores cannot be achieved by the small production of the germ-killing species. Safe and reproducible sterilization, especially even in cases of larger throughputs of items to be sterilized, cannot be achieved in practice with this method.

A known phenomenon is the sterilizing effect of plasma-generated gas, as is also described in US Patent Application 2010/0254853 A1. The effect of plasma-generated gas depends mainly on the generation of $NO_x$ and free radicals, with the associated long times of action of one hour and longer.

SUMMARY

The object of the present invention is to eliminate the disadvantages of the solutions described in the prior art.

The object is achieved according to the features of the claims. According to the invention, there is provided both a rapid and inexpensive method and a device for sterilization of items wherein:

a) the species having sterilizing action is generated in adequate amount, preferably using air,
b) efficient and gentle treatment even of structured items with narrow gaps and capillaries is possible, and
c) sterilization of items and substances can be achieved in a few seconds.

Surprisingly, it has been found that this method in particular is also suitable for cost-effective and efficient sterilization of inexpensive medical mass-produced products and packaging materials.

In the inventive method, the process of ionization of air as the process gas takes place spatially separated from the actual sterilization process, by the fact that the species active for sterilization are generated both in the ionization phase and in the ensuing recombination and cooling phase and only the plasma-activated gas mixture formed therefrom is used for sterilization, so that a direct plasma treatment does not take place.

DETAILED DESCRIPTION

The method for decontaminating and sterilizing objects and items is characterized by the following steps:
a) generating a plasma, preferably from air as process gas, which forms reactive nitrogen and oxygen species
b) oxidizing NO to $NO_2$, at temperatures below 400° C., so that a plasma-activated gas mixture with an $NO_2$ content of at least 0.3% is formed
c) bringing this plasma-activated gas mixture into contact with water in one or more of its states of aggregation
d) bringing the gas mixture generated in step c) into contact with the objects and items to be decontaminated or sterilized For this purpose, preferably dry air as process gas is passed through and partly ionized in a plasma source (for example of a microwave plasma) that preferably forms a volume plasma, wherein a hot plasma of air with a gas temperature of at least 1200° C. is formed, usually under atmospheric pressure during generation. After the plasma emerges from the excitation zone of the plasma source, the air plasma is subjected to specific cooling to bring about the formation of an activated plasma, which compared with the air used as starting gas has an $NO_2$ content of at least 0.3% after a certain reaction time.

Current practice is to specify, by numerical simulation, the cooling process as a function of the necessary starting species. Appropriate and known cooling mechanisms are applied to cool the plasma gas as required, but at least to below 400° C., and to form a plasma-activated gas mixture. $NO_2$ concentrations of typically between 0.3 and 5% are formed. By humidifying the plasma-activated gas mixture with water in one or more of its states of aggregation in a temperature range from −40° C. to 400° C., a partial reaction of water with components of the gas mixture is possible. The time of contact of the plasma-activated gas mixture with water may range from milliseconds to hours. This gas mixture formed by reaction with water (sterilizing gas mixture) and also the solution formed from the reaction of the plasma-activated gas mixture with water (sterilizing solution) may be used as sterilizing agents. The humidification of the plasma-activated gas mixture with water may be carried out as far as saturation.

The items to be sterilized are now exposed to the action of the gas mixture humidified with water for a specified period. For this purpose, either the sterilizing gas mixture humidified with water is passed over the items to be sterilized or the items are contained in a process chamber, into which the sterilizing gas mixture humidified with water is admitted. By inducing microcondensation of gaseous compounds on the cooler substrate surface, it is possible to shorten the treatment time and to increase the efficacy considerably. By using a nozzle at the outlet of the plasma source, the sudden expansion of the plasma gas after it emerges from the nozzle may be used for cooling and for microcondensation by lowering the temperature below the dew point. The items to be sterilized may also be used partly or completely for cooling the plasma gas or for microcondensation.

As a function of the desired degree of decontamination, the time of action (dwell time of the items to be sterilized in the sterilizing gas mixture) may be adjusted from approximately 2 seconds to 60 minutes, depending on the application.

The desired humidification with water may be adjusted by known devices, such as evaporators, bubblers, ultrasonic nebulizers, by injection of water or steam and by means of dosing ice or use of an ice maker. The reaction of the plasma-activated gas mixture with water may also take place in a buffer vessel partly filled with water, and the plasma-activated gas mixture may even be passed through the water.

After the end of the specified time of action, the process chamber is purged with sterile air until the air quality conforms to the permissible MAK values [maximum workplace concentrations]. The sterilizing gas may be disposed of by known appropriate measures, such as are achieved, for example, by using a gas scrubber or absorber material.

To improve the effect in narrow lumens and gaps, the process chamber may be evacuated before admission of the sterilizing gas mixture. By admitting the sterilizing gas mixture until atmospheric pressure and above is established, even narrow lumens and gaps are safely reached by the biocidal gas mixture. By applying a pressure change multiple times during the process of action of the sterilizing gas mixture (pressure-alternation technology), the sterilization process may be accelerated and the functional reliability improved, especially in cavities. By a larger number of pressure cycles, the pressure difference of the cycles may be reduced. In this way pressure-sensitive items may be treated.

Furthermore, the sterilizing gas may be passed through the process chamber and then returned to the plasma source, so that the concentration of the biocidal components of the plasma gas may be continuously increased to the necessary concentration in a circulation process.

For treatment of items that consist entirely or partly of cavities, the sterilizing gas may be admitted directly into or through the cavities.

A sterilizing gas mixture may also be generated by passing air through the sterilizing solution (15) that has already been prepared beforehand, resulting from the reaction of plasma-activated gas mixture with water, whereupon the humidified gas mixture formed in this way is used for sterilization.

It is also possible in principle to replace the plasma-activated gas mixture by a corresponding synthetic gas mixture.

A device for performing the method consists of a supply unit for air, a plasma source for generating a plasma, a device, particularly a cooling device, for oxidizing the air plasma emerging from the plasma source, a unit suitable for contacting a plasma-activated gas mixture with water or steam, particularly a humidifying device containing water, and a portion of the device, particularly a process chamber, for receiving the items to be decontaminated or sterilized. The device may be expediently supplemented by additionally disposing a vacuum pump or an air-circulation unit or a compressor for the sterilizing gas.

The plasma source may comprise an active plasma zone or an excitation zone in which air is ionized, e.g. by means of microwaves. The plasma source may also comprise an integrated cooling device configured to protect the solid components of the plasma from heat damage that may be caused by the generated plasma. Furthermore, the plasma source may comprises an isolation, particularly made of thermostable material such as, for example, ceramics, wherein particularly the isolation at least partially encloses the active plasma zone of the plasma source. Additionally, the cooling device for oxidizing the air plasma and the integrated cooling device of the plasma source may be supplied by different or the same coolant supply.

Within the meaning of the invention, the term "active plasma zone" or "excitation zone" refers to a cavity within the plasma source in which a gas is ionized or transformed into a plasma.

Particularly, the cooling device is spatially separated from the plasma source, or in other words, arranged outside of the plasma source, more particularly outside of the active plasma zone.

Within the meaning of the invention, the term "spatially separated" means that the cooling device is not build-in the plasma source so to cool the plasma source and a plasma generated and comprised within the plasma source.

Accordingly, the cooling device is particularly arranged such to the plasma source that the cooling device does not cool the plasma source, particularly not a plasma located within the plasma source, more particular in the active plasma zone. Particularly, cooling of the plasma source, particularly of the active plasma zone, by the cooling device would lead to a decrease of the concentration of the sterilizing species.

The plasma device may be fluidly connected to the cooling device by a means configured to guide a plasma generated in the plasma source into the cooling device. Such means may be a pipe connecting the plasma source and the cooling device. Such means may also be formed by an opening in the plasma source and an opening in the cooling device, wherein both opening are tightly connected.

Particularly, the plasma source may be a microwave-excited plasma source.

Particularly, the portion of the device suitable for receiving the object is or is designed as a process chamber. Such process chamber may be vacuum or pressure chamber. Additionally, the process chamber may be fluidly connected to a vacuum pump.

Furthermore, the process chamber may be fluidly connected to the supply unit or the plasma source. Advantageously, the plasma-activated gas mixture may be guided into the plasma source or the supply unit to achieve a higher concentration of biocidal species in the plasma-activated gas mixture.

Particularly, the unit suitable for contacting a plasma-activated gas mixture with water or steam may be a bubbler or a device suitable for injecting water or steam.

Additionally, the device of the invention may comprises a heating device configured to heat the plasma-activated gas mixture after being cooled in the cooling device, particularly to a temperature in the range of 60° C. to 1200° C., particularly in the range of 400° C. to 1200° C. The heating of the plasma-activated gas mixture may be performed stepwise or continuous in the heating device. Accordingly, the heating device may comprises one compartment, in which the plasma activated gas mixture is heated to the desired final temperature. Alternatively, the heating device may comprise more compartments, e.g. three compartments, in which the plasma activated gas mixture is stepwise heated to the desired final temperature.

Within the meaning of the invention, a gas mixture formed after ionization and subsequent recombination as well as cooling, which mixture contains new molecular compounds and radicals compared with the starting gas is to be understood as a plasma-activated gas mixture.

The advantages of the inventive method and device compared with the prior art are based in particular on the fact that very rapid inactivation of the microorganisms to the point of sterilization is made possible in a few seconds, that direct contact between the plasma and the substances and objects does not or does not have to take place, and that preferably only room air or ambient air is used as working gas together with water for generating the species important for decontamination. Thus even thermally labile substances can be treated without problems. By the additional combined action of gaseous and liquid (condensate) species, extremely short and highly effective treatment times are achieved for the items to be decontaminated or sterilized. In this way material damage may be largely avoided. By separating the plasma process from the sterilization process, direct action of the plasma on the material properties of the items to be sterilized is ruled out, as are also feedback effects on the plasma process, thus leading to a substantial improvement of process safety.

Extreme cooling of the sterilizing gas mixture to approximately 40° C. and lower therefore also permits much longer times of application to human subjects, for example for disinfection of wounds and for treatment of food products.

With the implementation of this method, it is possible for the first time to use a very hot air plasma with its high efficiency relative to the generation of antimicrobial species for sterilization, even of heat-sensitive and structured items, by the fact that the generation phase is separated from the phase of action by the interposed cooling process.

This method also operates extremely economically and efficiently, since, for example, a highly effective sterilizing gas mixture can be generated at a rate of up to approximately 4 m$^3$/h with air, which is free, as the working gas, and with small amounts of water, as well as with only one plasma source having a microwave power of approximately 2 kW. As an example, this permits surface decontamination at cycle times of approximately 2 s per surface. Since the plasma process and the sterilization process are separated from one another, several process chambers may be filled in succession with the sterilizing gas mixture using one plasma source. In this way, in the case of preforms, for example, the capability exists of disinfecting them either individually in a high-speed process or in large quantities in a batch process using one or more chambers.

Because of the great diffusion capability of the sterilizing gas mixture, even through gas-permeable packaging (Tyvek), structured items having narrow capillaries and gaps may be sterilized without problem.

The method may be used by scaling the injected power and disposing a plurality of plasma sources within a broad power spectrum, thus making it suitable for small to large sterilization volumes.

By the fact that storage of hazardous materials in the form of highly toxic substances is not necessary and that, by virtue of the nature of the process, only a small amount of sterilizing gas mixture is produced, the potential for danger to humans and the environment is extremely small even in the event of major damage to the system. Monitoring capability may be included in the system.

The rapid and highly efficient activity of the method has been demonstrated in several microbiological experiments.

The invention will be explained hereinafter on the basis of exemplary embodiments.

Figure 1:
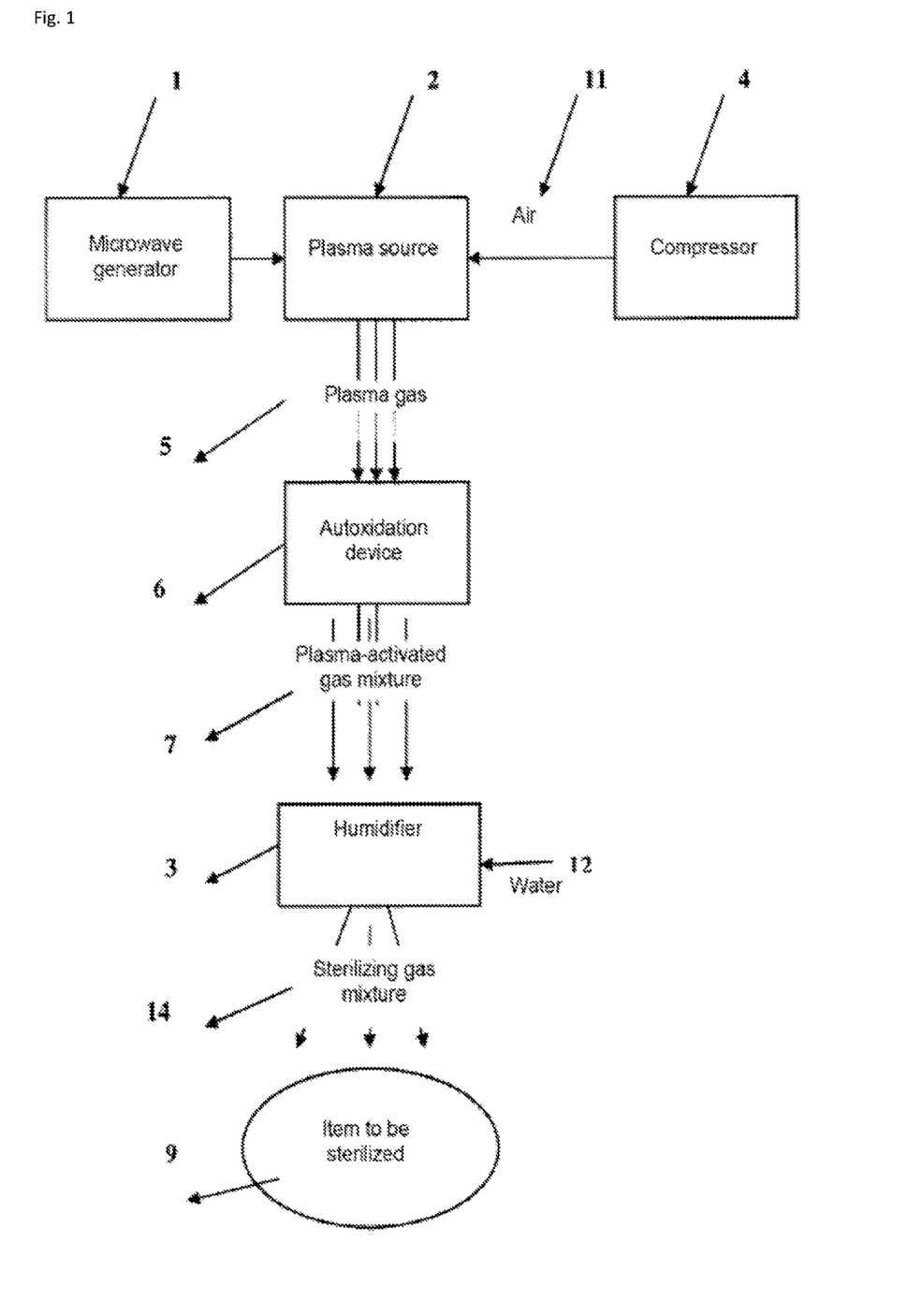
FIG. 1 shows a device by means of which a biocidal sterilizing gas mixture (14) is generated from air (11) as the process gas and the sterilizing gas mixture (14) circulates around the item (9) to be sterilized.

FIG. 1 shows a device by means of which a biocidal sterilizing gas mixture (14) is generated from air (11) as the process gas and the sterilizing gas mixture (14) circulates around the item (9) to be sterilized.

The device consists of a microwave generator (1), which supplies the plasma source (2) with microwave energy, of a plasma source (2), which generates a voluminous hot plasma (5) under atmospheric pressure, of a compressor (4), which forces the air (11) through the plasma source (2) and of a device (cooling device), in which NO (6) is oxidized and by means of which the hot plasma gas (5) emerging from the plasma source (2) is cooled to the point that the NO is oxidized to $NO_2$ and a plasma-activated gas mixture (7) is formed, which mixture is humidified with water (12) in the humidifier (3), whereby the sterilizing gas mixture (14) is formed, which mixture exposes the item (9) to be sterilized to its action by the fact that the sterilizing gas mixture (14) circulates around it.

Figure 2:
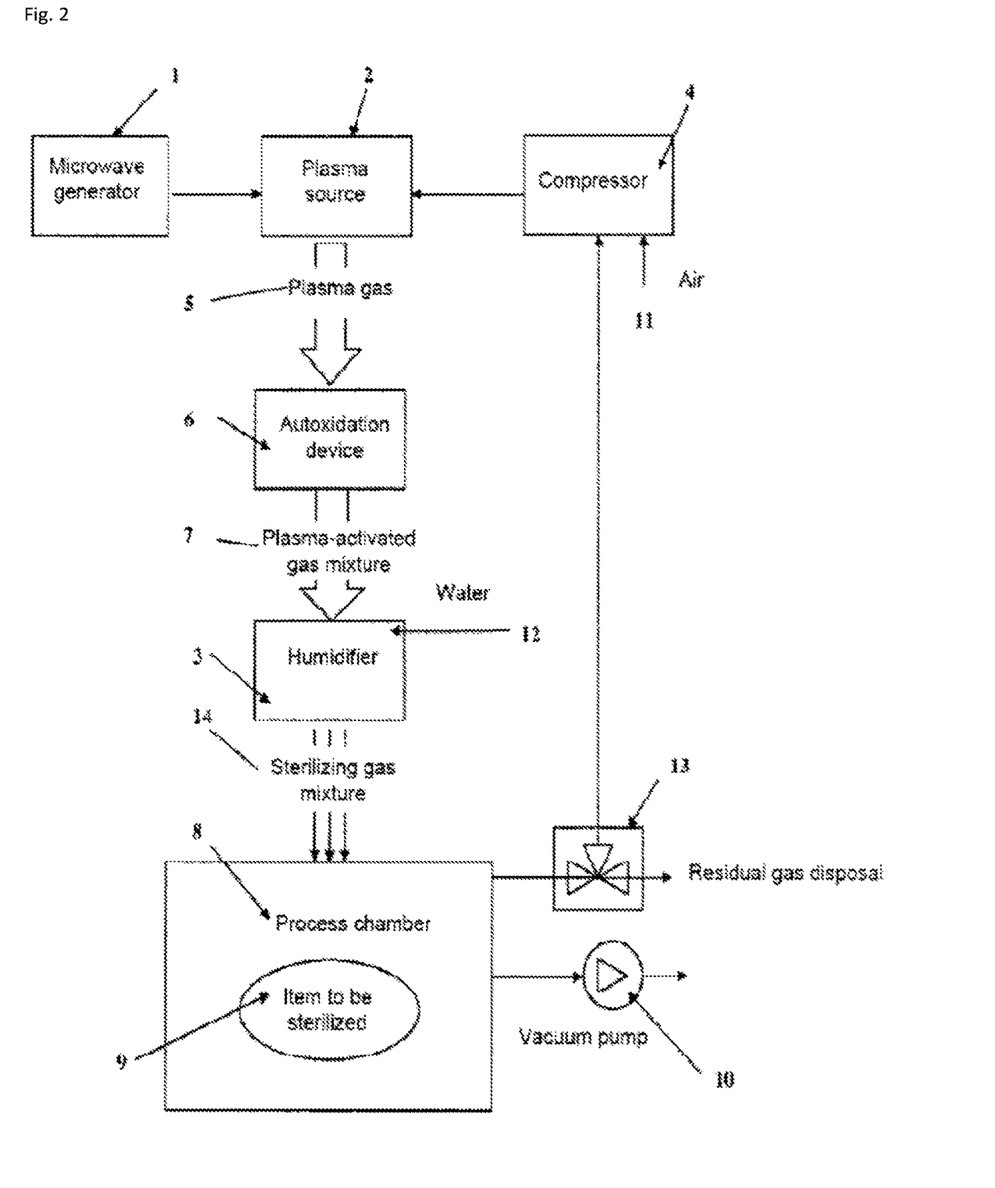
FIG. 2 shows a device by means of which a biocidal sterilizing gas mixture (14) is generated from air (11) as the process gas and the item (9) to be sterilized is exposed to the action of the sterilizing gas mixture (14) in a process chamber (8).

FIG. 2 shows a device by means of which a biocidal sterilizing gas mixture (14) is generated from air (11) as the process gas and the item (9) to be sterilized is exposed to the action of the sterilizing gas mixture (14) in a process chamber (8).

The device consists of a microwave generator (1), of a plasma source (2), of a compressor (4), of a humidifier (3), of a device for oxidizing NO (6), of a process chamber (8), of a vacuum pump (10) and of a control and regulating unit (13).

The microwave generator (1) supplies the plasma source (2) with microwave energy, so that a hot plasma (5), preferably under atmospheric pressure, is generated from the supplied air (11).

By means of the device for oxidizing NO (6), the plasma gas (5) emerging from the plasma source (2) is cooled within a specified time to the point that a plasma-activated gas mixture (7) with an $NO_2$ content of at least 0.5% is formed. This plasma-activated gas mixture (7) is humidified with water (12) in a humidifier (3), so that a sterilizing gas mixture (14) is formed, which mixture is admitted into a process chamber (8), in which the item (9) to be sterilized is contained. The process chamber (8) may be evacuated completely or partly by means of a vacuum pump (10) and filled with the sterilizing gas mixture (14), so that the item (9) to be sterilized may be exposed to the action of the sterilizing gas mixture (14) for a preset time.

This operation may be repeated several times, in order especially to sterilize items with narrow capillaries and gaps safely. The item (9) to be sterilized may be exposed to the action of the sterilizing gas mixture (14) even if it is contained in sterile packaging comprising a gas-permeable membrane (Tyvek). It is also possible to allow the sterilizing gas mixture (14) to flow through the process chamber (8) and then to dispose of it, or else to return the sterilizing gas mixture (14) via a control and regulating unit (13) in circulation through the plasma source (2), so that a higher concentration of biocidal species may be achieved in the sterilizing gas mixture (14).

Figure 3:
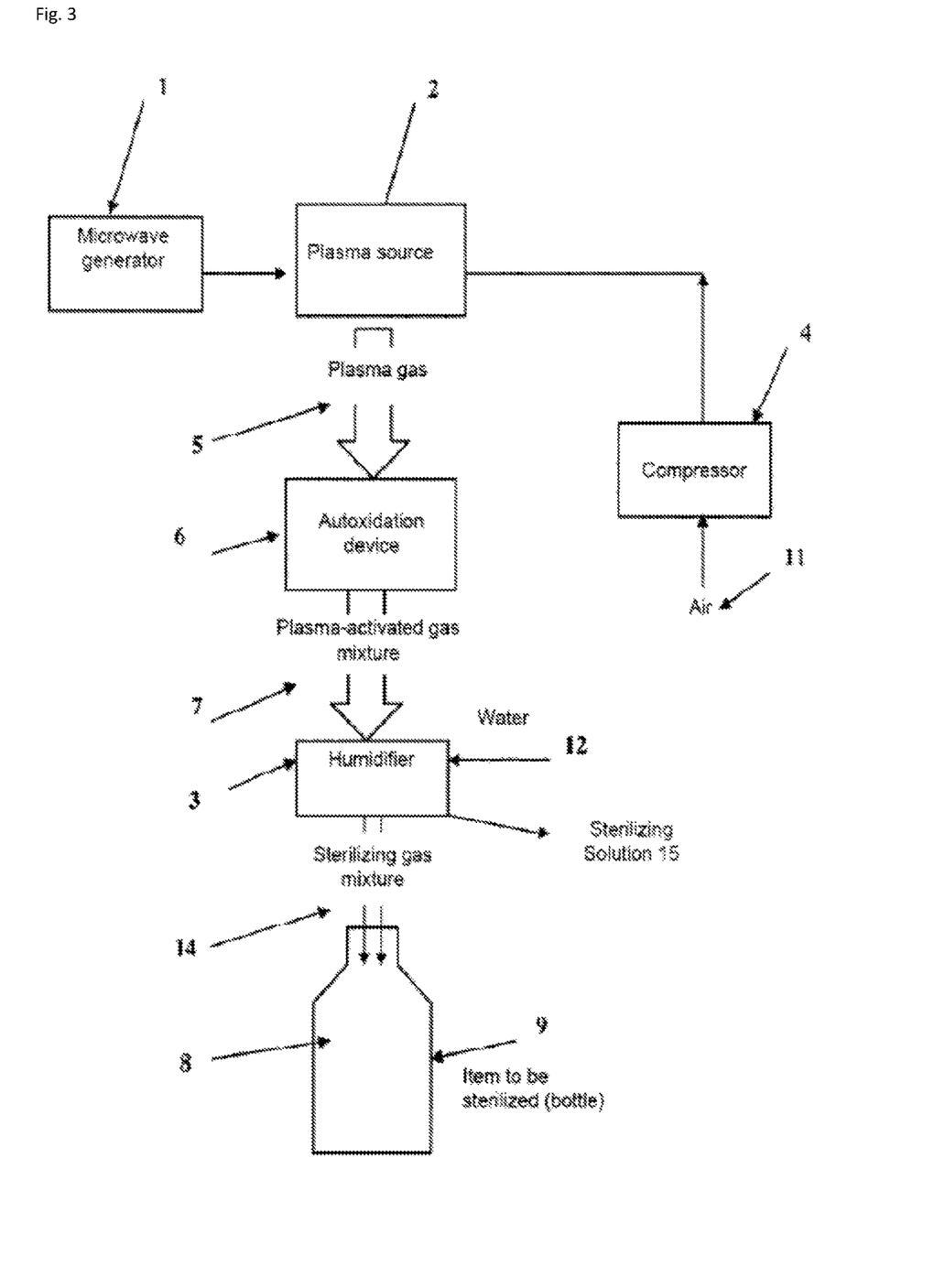
FIG. 3 shows a device that generates a biocidal sterilizing gas mixture (14) and a sterilizing solution (15) by means of a plasma source (2), together with a process chamber (8) that consists of the item (9) to be sterilized itself.

FIG. 3 shows a device that generates a biocidal sterilizing gas mixture (14) and a sterilizing solution (15) by means of a plasma source (2), together with a process chamber (8) that consists of the item (9) to be sterilized itself.

The device consists of a microwave generator (1), of a plasma source (2), of a compressor (4), of a humidifier (3), of a device for oxidizing NO (6) and of a process chamber (8).

Thus the process chamber (8) may also be formed partly or entirely of the item (9) to be sterilized itself, for example containers and tubing. Such containers and tubing may be, for example, canisters, beakers, bottles, and tubes and medical products, such as endoscopes and catheters.

Figure 4:
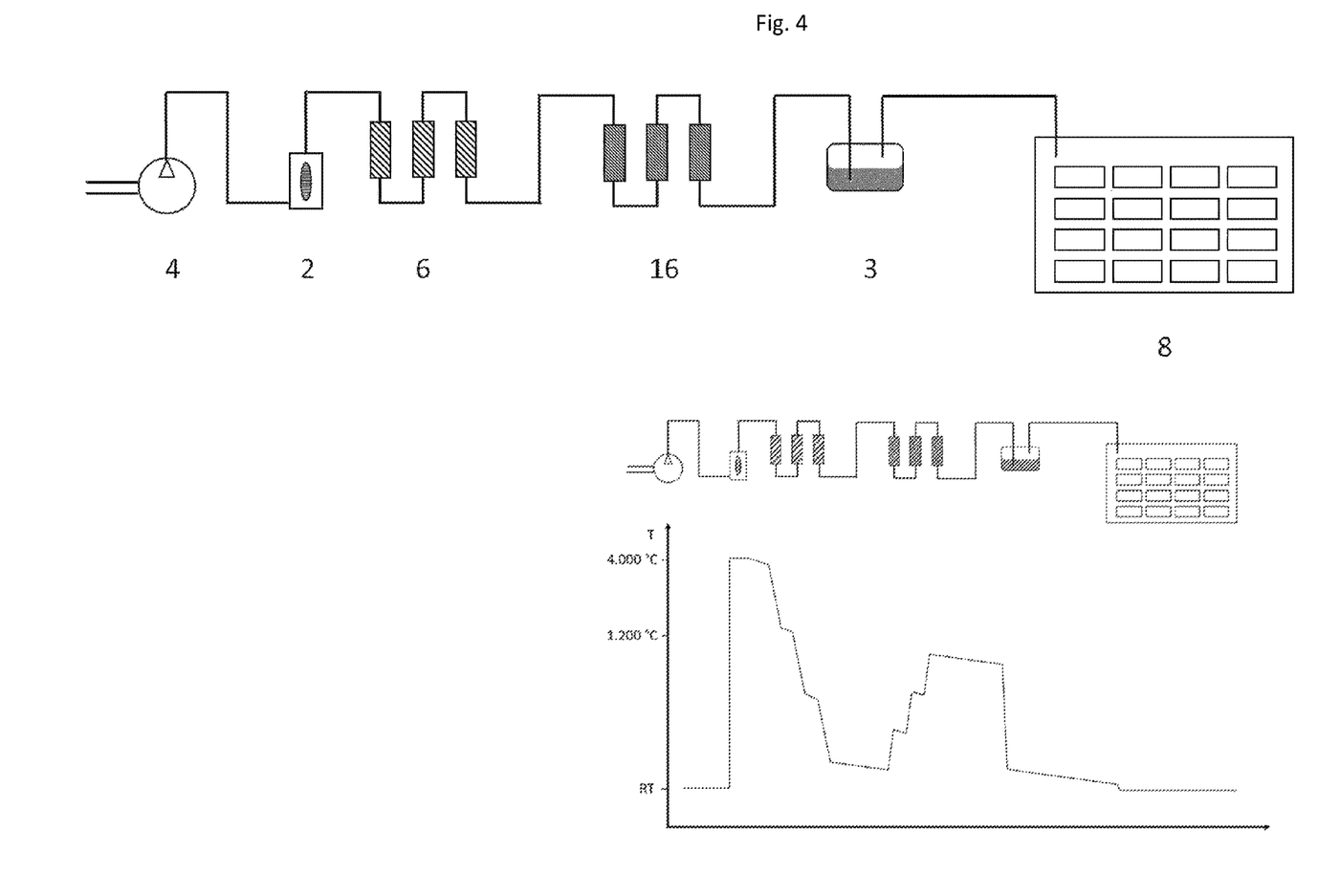
FIG. 4 shows a further embodiment of the device of the invention further comprising a heating device or thermal conditioner (16), which is arranged between the cooling device (6) and the humidifier (3). Also shown is a temperature profile of the plasma activated gas mixture.

FIG. 4 shows a further embodiment of the device of the invention further comprising a heating device or thermal conditioner (16), which is arranged between the cooling device (6) and the humidifier (3).

Figure 7:
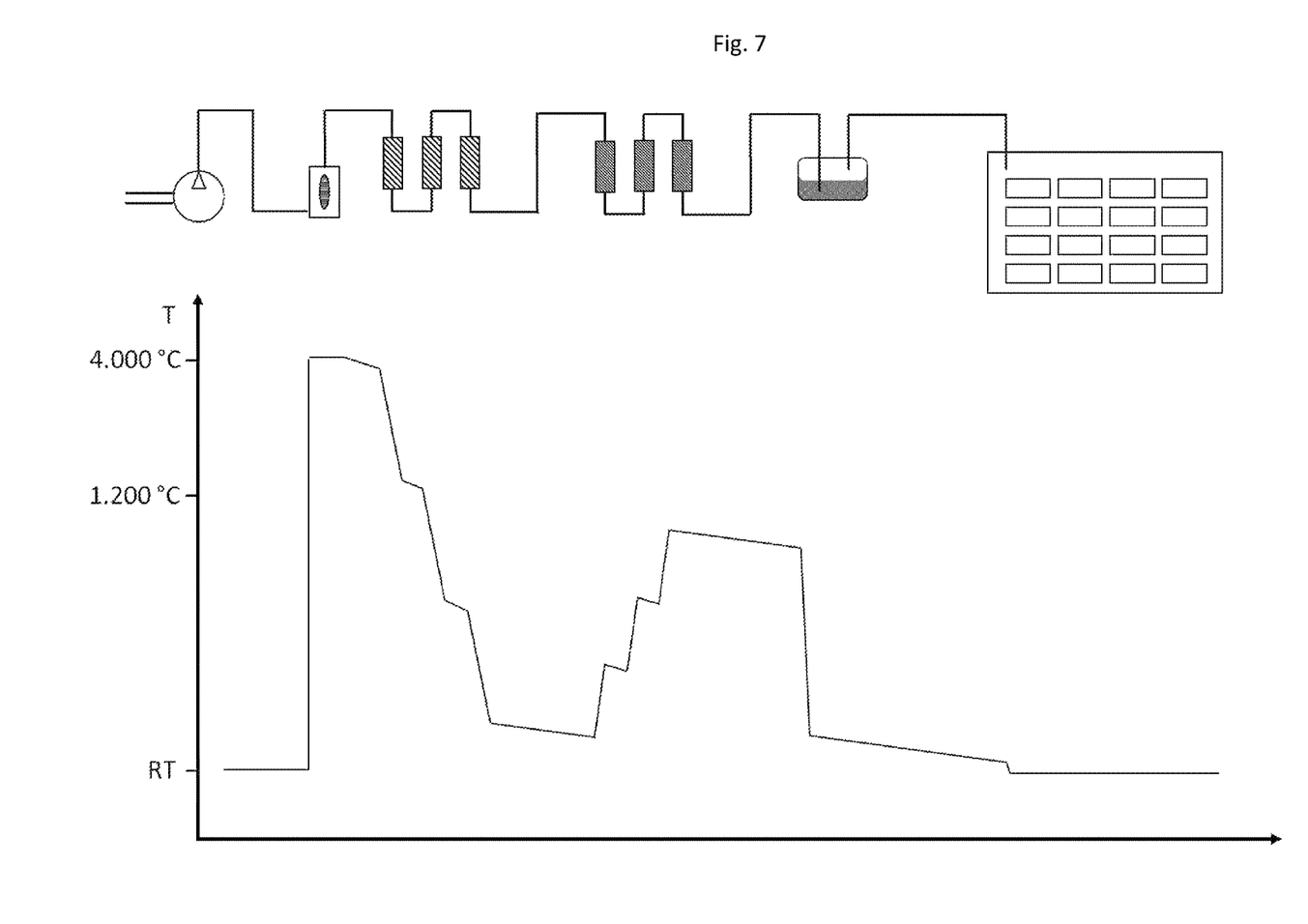
FIG. 7 shows an enlarged view of the temperature profile of the plasma activated gas mixture.

The thermal conditioner (16) is configured to the receive the plasma activated gas mixture after being cooled below 400° C., particularly to a temperature in the range of 15° C. to 40° C., more particular to 20° C., and to heat the cooled plasma-activated gas mixture, particularly to a temperature in the range of 60° C. to 1200° C., more particular to temperature in the range of 400° C. to 1200° C., and to guide the heated plasma activated gas mixture to the humidifier. Also shown in FIG. 4 is a temperature profile of the plasma activated gas mixture. Air supplied by a compressor (4) is guided into the plasma source (2), transformed therein into an air plasma having a temperature above 1200° C., e.g. approx. 4000° C., the plasma is guided through the cooling device under cooling below 400° C., e.g. ambient temperature yielding a plasma-activated gas mixture, which is then guided through the heating device or thermal conditioner (16) under heating to a temperature between 60° C. and 1200° C., e.g. to approx. 1000° C., the heated plasma or plasma activated gas mixture is humidified and cooled in the humidifier (3), to a temperature below 400° C., particularly to temperature between 40° C. and ambient temperature, and the humidified plasma-activated gas mixture is guided in the process or treatment chamber (8), in which an item to sterilized is contacted with the humidified plasma-activated gas mixtures. An enlarged view of the temperature profile is depicted in FIG. 7.

Figure 5:
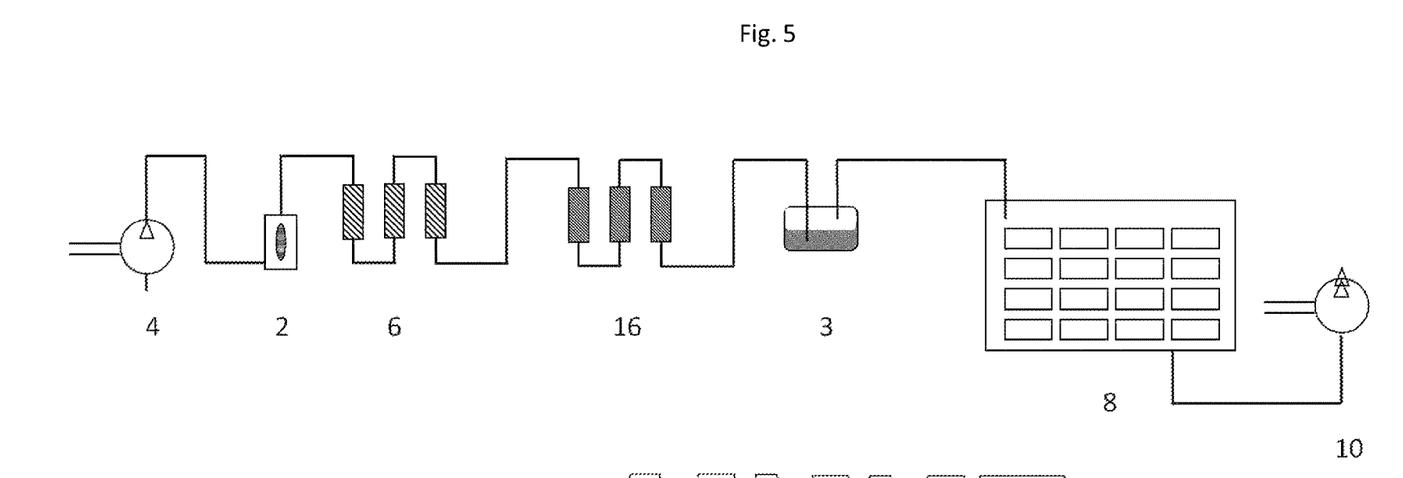
FIG. 5 shows a further embodiment of the device of the invention.

FIG. 5 shows a further embodiment of the device of the invention.

As illustrated in FIG. 5, the process or treatment chamber (8) may be connected with a vacuum pump (10). The vacuum pump (10) allows an evacuation of the process or treatment chamber (8) with the item to sterilized placed in the chamber (8), particularly before the humidified plasma-activated gas mixtures is admitted into the process chamber (8).

Figure 6:
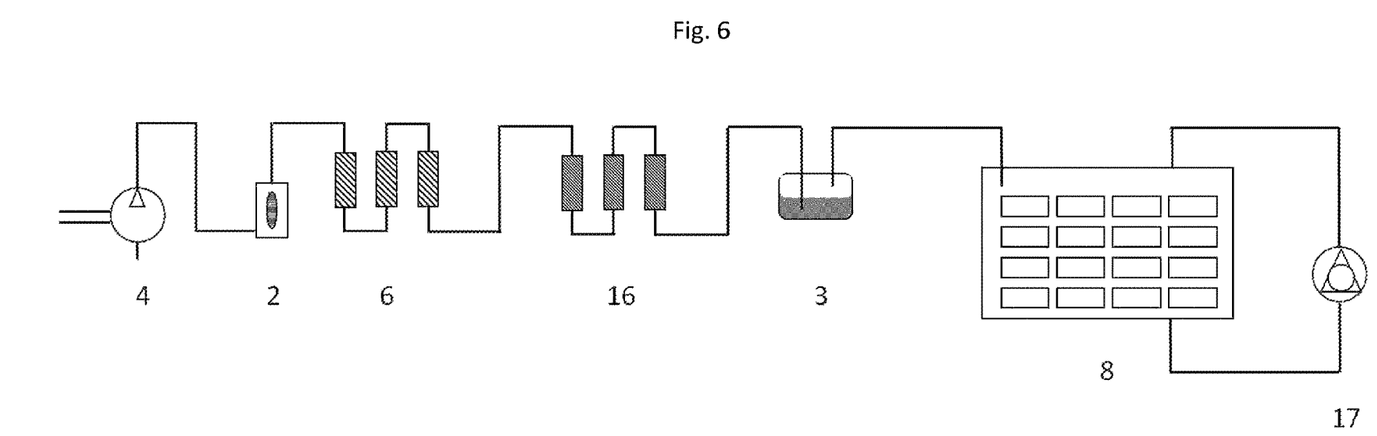
FIG. 6 shows a further embodiment of the device of the invention.

FIG. 6 shows a further embodiment of the device of the invention.

Alternatively, the process or treatment chamber (8) may be connected with a circulation system with a radial fan as depicted in FIG. 6. The circulation system allows the circulation of the humidified plasma or plasma activated gas mixture, thereby increasing the efficiency of the treatment or sterilization of the item with the mixture.

After the treatment process is completed, the circulation systems allows to remove the process gas out of the treatment chamber and to deliver it to an exhaust system whereas the chamber is flooded with fresh air in the same time.

EXAMPLES

Example 1

Experiment to Demonstrate the Antimicrobial Action of the Plasma-Activated Gas Mixture An experiment is described hereinafter. Several variations are possible, and the microbicidal effectiveness of the method is presented for some of those in Table 1.

Decontamination of various vegetative and sporulated microorganisms by a sterilizing gas mixture, generated by using dry or humidified air (NO, NO2) and a microwave plasma.

Glass laboratory bottles of 250 mL capacity were used as reaction chambers and thus as test specimens. The test specimens were contaminated by spraying. The treatment was applied after the test specimens had been dried. The starting concentration in each case was $10^8$ CFU/mL. The evaluation was carried out with standardized methods after varied times of action from 10 seconds to 60 minutes.

Figure 8:
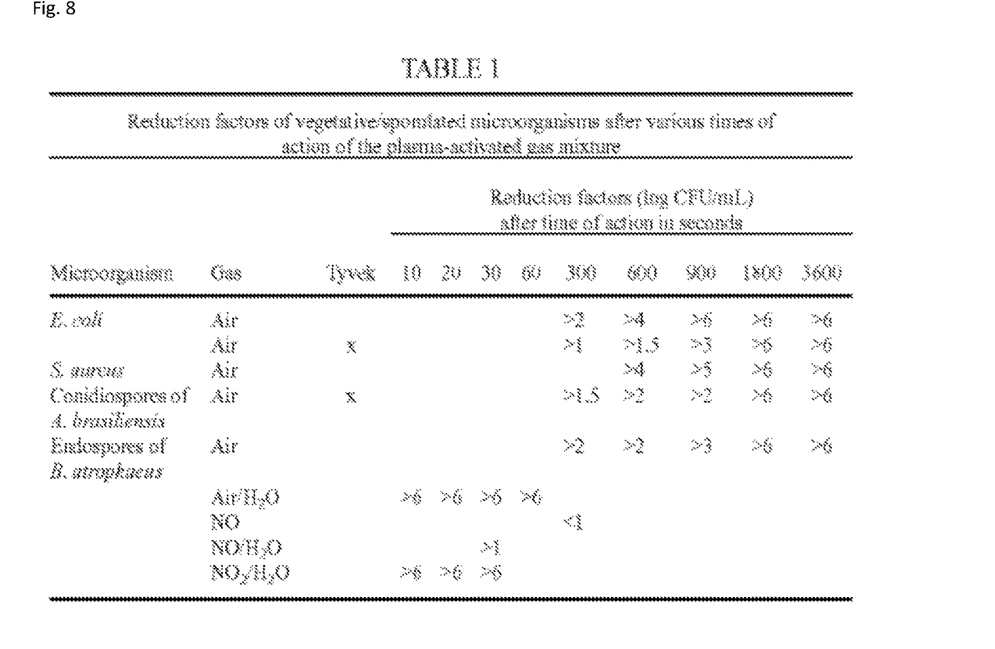
FIG. 8 is a Table showing Reduction Factors of vegetative/sporulated microorganisms after various times of action of the plasma-activated gas mixture.

The reduction factors shown in log steps (CFU/mL) in Table 1 as depicted in FIG. 8 were detected after the various times of action. Reduction factors are the difference between the logarithm of the control (log CFU) and the logarithm of the number of colony-forming units of the sample after the action of the plasma-activated gas. The limit of detection was $10^{-1}$.

The experiments reveal acceleration of the microbial inactivation by a factor of >10 when water is used. In addition, the importance of $NO_2$ is clearly evident. The gas mixture with antimicrobial action may be produced by means of plasma or synthetically for the inactivation to be achieved. Diffusion barriers such as Tyvek, for example, slow but do not inhibit the inactivation. Variation of the test specimens had a retarding influence only at increasing complexity.

LIST OF REFERENCE NUMERALS

1 Microwave generator
2 Plasma source
3 Humidifier
4 Compressor
5 Hot plasma
6 Cooling device
7 Plasma-activated gas mixture
8 Process chamber
9 Item to be sterilized
10 Vacuum pump
11 Air
12 Water
13 Control and regulating device
14 Sterilizing gas mixture
15 Sterilizing solution
16 Thermal conditioner
17 Circulation system with radial fan

We claim:

1. A device, comprising:
 a supply device suitable for supplying air,
 a plasma source suitable for generating a plasma having a gas temperature of at least 1200° C.,
 a cooling device compartment suitable for cooling the plasma to a gas temperature below 400° C. and oxidizing a plasma gas, wherein said cooling device compartment is spatially separated from the plasma source,
 a unit suitable for contacting a plasma-activated gas mixture with water or steam, and
 a portion of the device suitable for receiving an object to be sterilized, wherein the device is suitable for decontaminating and sterilizing the object by a method comprising
  generating a plasma having a gas temperature of at least 1200° C. from air as a process gas, thereby obtaining reactive nitrogen and oxygen species,
  cooling the plasma to a temperature below 400° C. and oxidizing NO to $NO_2$, thereby obtaining a plasma-activated gas mixture with an $NO_2$ content of at least 0.3%,
  contacting the plasma-activated gas mixture with water in at least one state of aggregation of the water, and subsequently contacting the gas mixture with an object in need thereof;
 wherein said cooling device compartment is arranged between said plasma source and said portion suitable for receiving an object to be sterilized, and
 said device is configured to guide a plasma generated in said plasma source into said cooling device compartment.

2. The device according to claim 1, wherein the plasma source is a microwave-excited plasma source.

3. The device of claim 1, wherein the portion of the device suitable for receiving the object is a process chamber.

4. The device according to claim 3, wherein the process chamber is a vacuum and pressure chamber.

5. The device according to claim 3, wherein the process chamber is fluidly connected to a vacuum pump.

6. The device according to claim 3, wherein the process chamber is fluidly connected with the supply device or the plasma source.

7. The device of claim 1, further comprising a nozzle at an outlet of the plasma source.

8. The device of claim 1, wherein the unit is a bubbler or a device suitable for injecting water or steam.

9. The device of claim 1, wherein the cooling device compartment is spatially separated from a plasma comprised within the plasma source.

10. The device of claim 1, wherein the cooling device compartment is arranged to the plasma source such that the cooling device does not cool the plasma source.

11. The device of claim 1, wherein the plasma source is fluidly connected to the cooling device compartment by a means configured to guide a plasma generated in the plasma source into the cooling device compartment.

12. The device of claim 1, further comprising a heating device, wherein the heating device is configured to heat the plasma-activated gas mixture after being cooled in the cooling device compartment, wherein said heating device is arranged between said cooling device compartment and said portion suitable for receiving an object to be sterilized.

13. The device of claim 1, wherein the device is configured to guide at least one part of the plasma-activated gas mixture before or after being contacted with water or steam into the plasma source or the supply unit.

\* \* \* \* \*